US00PP12346P2

(12) United States Plant Patent
Drewlow

(10) Patent No.: US PP12,346 P2
(45) Date of Patent: Jan. 8, 2002

(54) NEW GUINEA IMPATIENS PLANT NAMED 'OVATION SALMON PINK SWIRLS'

(75) Inventor: Lyndon W. Drewlow, Santa Barbara County, CA (US)

(73) Assignee: Oglevee Limited, Connellsville, PA (US)

( * ) Notice: Subject to any disclaimer, the term of this patent is extended or adjusted under 35 U.S.C. 154(b) by 0 days.

(21) Appl. No.: 09/550,511

(22) Filed: Apr. 17, 2000

(51) Int. Cl.[7] ..... A01H 5/00
(52) U.S. Cl. ..... Plt./318
(58) Field of Search ..... Plt./318

*Primary Examiner*—Bruce R. Campell
*Assistant Examiner*—Anne Marie Grünberg
(74) *Attorney, Agent, or Firm*—Webb Ziesenheim Logsdon Orkin & Hanson, P.C.

(57) ABSTRACT

A distinct cultivar of Impatiens plant named Ovation Salmon Pink Swirls, characterized by its salmon-pink flower color, large flower diameter, deep green leaves, continuous and long-lasting flowering, self-branching, and vigorous habit.

1 Drawing Sheet

The present invention relates to a new and distinctive cultivar of Impatiens plant, botanically known as *Impatiens Hawkeri,* commercially known as New Guinea Impatiens, and known by the cultivar name 'Ovation Salmon Pink Swirls'. Ovation Salmon Pink Swirls was developed in a controlled breeding program by crossing Mikkelsen Seedling No. 95-1105-9 (seed parent) with Mikkelsen Seedling No. 95-1105-1 (pollen parent). Both parents are proprietary breeding lines which have not been sold or made publicly available in this country.

Asexual reproduction carried out by the inventor in Lompoc, Calif. by terminal or stem cuttings has shown that the unique features of this new Impatiens are stabilized and are reproduced true to type in successive propagations.

The following combination of characteristics distinguish the new Impatiens from both its parent varieties and other cultivated Impatiens of this type known and used in the floriculture industry:

1. Ovation Salmon Pink Swirls has flowers colored Red Group 43C, Harmony Peach (unpatented) has Red Group 52C flowers, and Celebration Light Salmon (U.S. Plant Pat. No. 9,213) has Red Group 48B flowers. All three have Orange Group 27D in the center of the flower, each with a different pattern.

2. Both Harmony Peach and Celebration Light Salmon have carmine coloration at the center of the flower, while Ovation Salmon Pink Swirls does not.

3. Ovation Salmon Pink Swirls has a larger flower diameter (7.0 to 7.5 cm) than both Harmony Peach and Celebration Light Salmon (6.0 to 6.5 cm).

4. Ovation Salmon Pink Swirls has a mounded growth habit while Harmony Peach is more upright with Celebration Light Salmon being upright and taller growing.

5. Ovation Salmon Pink Swirls has deep green leaves, Harmony Peach has lighter green leaves, and Celebration Light Salmon having lighter green, variegated leaves.

6. Ovation Salmon Pink Swirls has shorter leaves (7 to 8 cm long), while Celebration Light Salmon has longer leaves (8 to 9 cm), and Harmony Peach has the longest leaves (11 to 12 cm).

7. The spur of Ovation Salmon Pink Swirls is light red-purple with a green tip which his 3.5 cm in length, as compared to Celebration Light Salmon, which is a deep red-purple with a green tip and 4.5 to 5.0 cm long, and Harmony Peach, which his lighter red-purple with a red-purple tip and 4.5 to 5.0 cm long.

8. Pedicels on Ovation Salmon Pink Swirls are green, while the pedicels on Celebration Light Salmon and Harmony Peach have a red-purple cast.

9. Ovation Salmon Pink Swirls has an intermediate amount of red pigmentation in the stem, while Celebration Light Salmon has less, and Harmony Peach has more.

The accompanying colored photograph illustrates the overall appearance of this cultivar taken as a face view of the plant and showing the colors as true as it is reasonably possible to obtain in a colored reproduction of this type.

The following is a detailed description of my new cultivar, based on plants produced in greenhouses in Lompoc, Calif. during the Fall–Winter season of the year. Plants were grown in 15 cm pots and measurements were taken 20 weeks after rooted cuttings were planted. Height measurements were taken from the soil line of the container. The plants were grown at 16° C. night temperatures, under 3000 to 4000 foot candles of light and 200 ppm nitrogen, 75 ppm potassium, and 200 ppm phosphorous with nutritional elements added. Habit of growth, foliage coloration, leaf variegation, size of leaves, and flower size will be greatly influenced by nutritional and environmental conditions.

Color references are made to The Royal Horticultural Society Colour Chart except where general terms of ordinary dictionary significance are used.

Parentage: A controlled cross between female parent Mikkelsen Seedling No. 95-1105-9 and male parent Mikkelsen Seedling No. 95-1105-1.

Propagation:

(*A*) *Type cutting.*—Stem tip 15 mm long will develop to 4 to 5 cm long in 18 to 21 days.

(*B*) *Time to root.*—8–10 days at 23° C. summer; 10–12 days at 20° C. winter.

(*C*) *Rooting habit.*—Heavy, fiborous.

Plant description:

(*A*) *Form and habit of growth.*—Mounded, self-branching, intermediate in height, flowers open over the top of leaf canopy; continuous flowering herb; vigorous growing. Average height is 17 to 20 cm and average width is 35 to 40 cm. Internode length is 3 to 4 cm depending upon growing environment. Pedicel is Yellow-Green Group 148C, stem is Yellow-Green Group 147C, and internode is Yellow-Green Group 147C.

(*B*) *Foliage description.*—Dark green; light green midrib, and no leaf variegation. (1) Size: 7 to 8 cm long and 3.5 to 4 cm wide on average mature leaf. (2) Shape: Lanceolate with acuminate apex and acute base. (3) Texture: Both upper and lower surfaces are glabrous. (4) Margin: Entire, with fine cilia. (5) Color: Young foliage, top side is Yellow-Green Group 147A, underside is Yellow-Green Group 147B. Mature foliage, top side is Yellow-Green Group 147A, underside is Yellow-Green Group 147B. (6) Venation: Pinnate, upper side and lower side are both Yellow-Green Group 148B. (7) Upper midrib is Yellow-Green Group 148C with Red-Purple Group 60D tint and lower midrib is Yellow-Green Group 148C.

*Branching.*—The branching is naturally occurring. Lateral branching at base: 10 or more lateral branches, starting at the base, and then from each leaf whorl; age of plant will determine the number of lateral branches. Lateral branch length is 10 to 15 cm, depending on location.

Flowering description:

(*A*) *Flowering habits.*—Flowers continuously from leaf whorl in a progressively orderly manner with one flower per leaf axil. When the last flower in a whorl opens the first flower in the whorl above starts to open. It takes 5 to 7 days for a mature bud to fully open and the flower may last two weeks or longer depending on the environment. The time to first flower is approximately 8 weeks from root cuttings. The flowers are self-cleaning.

(*B*) *Natural flowering season.*—Indeterminant and continuous; quantity of flowering increases with increasing levels of light.

(*C*) *Flower bud.*—Ellipsoidal; flowers perfect; red-purple spur with a green tip that is 3.5 cm long on mature bud, with the throat behind the ovary and originating from the major sepal. Bud length is 15 to 18 mm just before opening and bud diameter is 10 to 12 mm. Spur is Red-Purple Group 61B, spur tip is Yellow-Green Group 147B, and flower bud is Red Group 43D just before opening.

(*D*) *Flowers borne.*—On individual green pedicels 3.0 cm long from a whorl of usually three leaves. Flowering progressively around the whorls as buds and leaves develop. Leaf axils have one flower each.

(*E*) *Quantity of flowers.*—Numerous because of self-branching nature of plant and the long-lasting flower characteristic.

(*F*) *Diameter of flower.*—7.0 to 7.5 cm. Flower Depth: 6 mm.

(*G*) *Petals.*—(1) Shape: Heart. (2) Color: Top side in winter when opening is Red Group 43C with center of the flower being Orange Group 27D radiating into the petals; fading to larger areas of Orange Group 27D; underside is Red Group 48B. (3) Number of petals: Five. (4) Size of petals: Standard: 5.0 cm wide and 3.0 cm long, two unequal lobes with shallow cut. Wings: 4.0 cm wide and 3.5 cm long, two unequal lobes with moderate cut. Keel: 4.5 cm wide and 3.5 cm long, two unequal lobes with moderate cut.

(*H*) *Reproductive organs.*—(1) Stamens: Five in number. (a) Anther: Hooded shape, color is Yellow-White Group 158B with a Red Group 43C cast. (b) Pollen color: Yellow-White Group 158C. (2) Pistils: (a) Stigma: Five, segmented column, color is White Group 155B. (b) Style color: White Group 155B. (c) Ovaries: Five in number, size is 7 mm when immature, color is Yellow-Green Group 146A.

Disease resistance: No significant disease or insect problems seen to date.

(*I*) *Fertility.*—The plants are fertile, but do not normally set seed under greenhouse or garden conditions, unless in a controlled crossing program.

OTHER IMPORTANT CHARACTERISTICS

1. Self-branching, early flowering nature allows cultivar to be grown in 10 cm pots but is also vigorous enough to be grown in 15 to 25 cm containers as well.

2. Minimal fading of older flowers; large overlapping petals result in a round flower that produces an attractive floral display.

3. Has shown the ability to tolerate both high temperatures and full sun and continue to bloom as demonstrated in Connellsville, Pa. summer trials and to bloom as well with cool night temperatures (5 to 10° C.) as demonstrated in outdoor trials in Lompoc, Calif., thus, extending the growing season.

I claim:

1. A new and distinct variety of Impatiens plant named Ovation Salmon Pink Swirls, as illustrated and described.

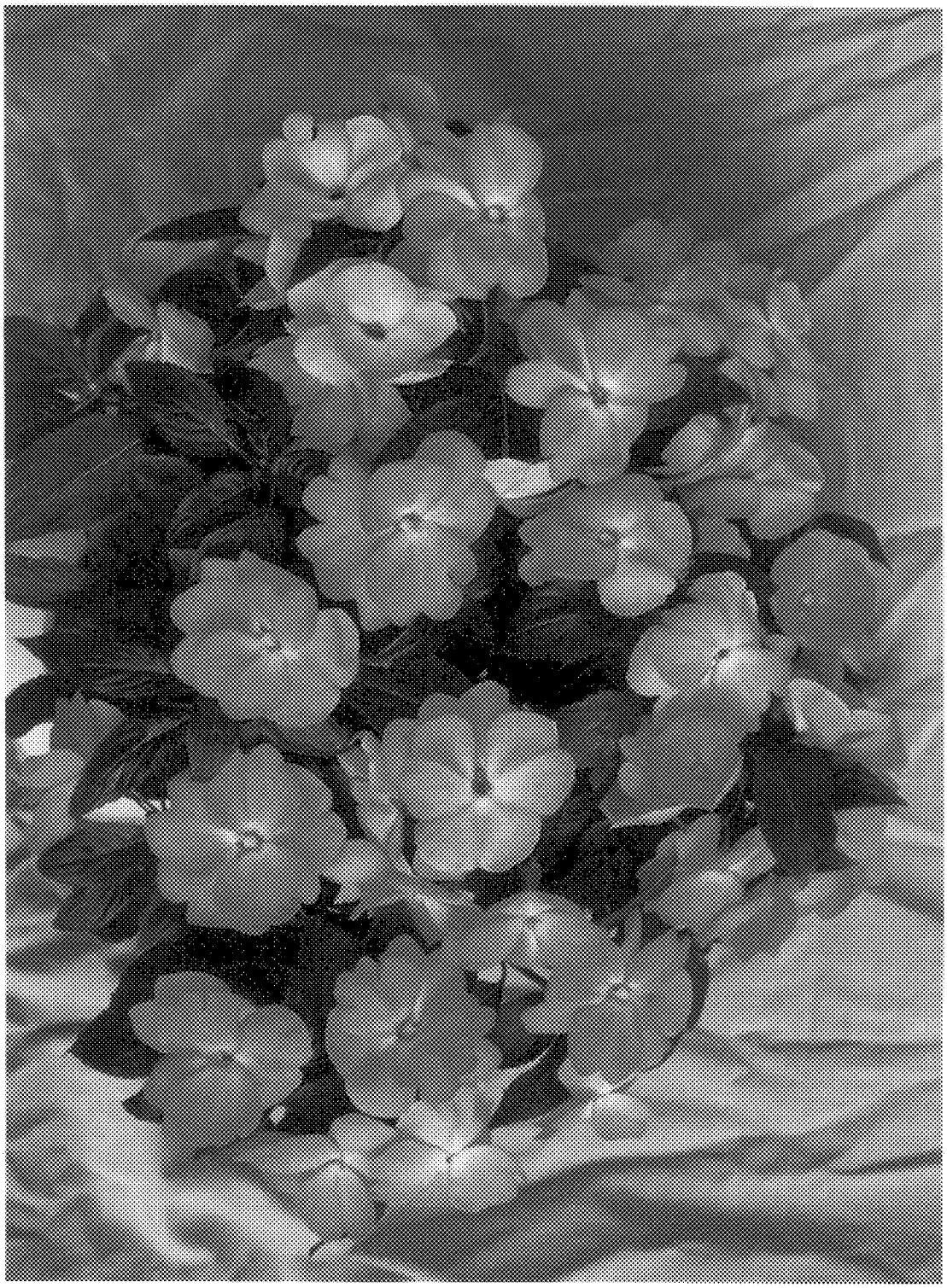

* * * * *